United States Patent

Teach

[11] 4,400,202
[45] Aug. 23, 1983

[54] N-M-PHENYL GLUTARIMIDE DERIVATIVES AND THEIR USE AS HERBICIDES

[75] Inventor: Eugene G. Teach, El Cerrito, Calif.

[73] Assignee: Stauffer Chemical Company, Richmond, Calif.

[21] Appl. No.: 330,630

[22] Filed: Dec. 14, 1981

Related U.S. Application Data

[60] Division of Ser. No. 232,330, Feb. 6, 1981, abandoned, which is a continuation of Ser. No. 910,405, May 30, 1978, abandoned.

[51] Int. Cl.³ ............... A01N 43/40; C07D 211/88
[52] U.S. Cl. ........................... 71/94; 71/95; 546/220; 548/545
[58] Field of Search ............ 546/220; 71/94, 95; 260/326.41

[56] References Cited

U.S. PATENT DOCUMENTS 4,031,088  6/1977  Ackerman ............... 546/220 X

Primary Examiner—Richard A. Schwartz
Attorney, Agent, or Firm—Michael J. Bradley

[57] ABSTRACT

Compounds defined by the generic formula

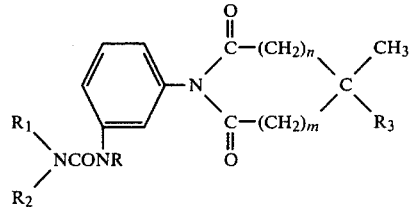

wherein R is hydrogen or hydroxyl, $R_1$ is selected from the group consisting of methyl and hydrogen; $R_2$ is selected from the group consisting of $C_1$–$C_4$ alkyl including methyl, ethyl, propyl and butyl and methoxy; $R_3$ is selected from the group consisting of hydrogen, methyl and ethyl; m is 0 or 1; and n is 1 or 2, exhibit herbicidal activity.

15 Claims, No Drawings

N-M-PHENYL GLUTARIMIDE DERIVATIVES AND THEIR USE AS HERBICIDES

This is a division, of application Ser. No. 232,330, filed Feb. 6, 1981 abandoned which is a continuation of application Ser. No. 910,405, filed May 30, 1978 now abandoned.

BACKGROUND OF THE INVENTION

Various N-phenylsuccinimide derivatives are disclosed in the prior art having broad antimicrobial properties in U.S. Pat. No. 3,741,981. Compounds disclosed are antimicrobial N-phenylsuccinimides of the formula

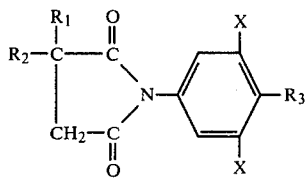

wherein $R_1$ and $R_2$ represent individually a hydrogen atom, an alkyl group having 1 to 3 carbon atoms, a benzyl group or a phenyl group, which may have been substituted by a chlorine atom; $R_3$ represents a hydrogen atom, a halogen atom or a methyl group; and X represents individually a halogen atom, provided that in case all of $R_1$, $R_2$ and $R_3$ are hydrogen atoms at the same time, X represents other halogen atoms than chlorine atoms.

No alkyl or alkyloxy succinimidophenyl or glutarimidophenyl urea derivatives are disclosed therein.

BRIEF DESCRIPTION OF THE INVENTION

This invention relates to a novel class of succinimidophenyl and glutarimidophenyl ureas and to their use as herbicides when used in a herbicidally effective amount. More specifically, this invention relates to succinimidophenyl and glutarimidophenyl ureas having the formula

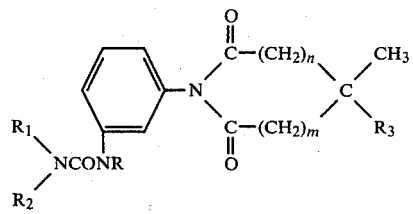

wherein R is hydrogen or hydroxyl, $R_1$ is selected from the group consisting of methyl and hydrogen; $R_2$ is selected from the group consisting of $C_1$–$C_4$ alkyl including methyl, ethyl, propyl and butyl and methoxy; $R_3$ is selected from the group consisting of hydrogen, methyl and ethyl; m is 0 or 1; and n is 1 or 2, which exhibit herbicidal activity.

The compounds of the present invention, as will be seen from the data which follows, have utility as both pre-emergence and post-emergence herbicides, against a wide range of plant species.

The term "herbicides", as used herein, means a compound which controls or modifies the growth of plants By "plants" is meant germinant seeds, emerging seedlings and established vegetation, including roots and above ground portions. Such modifying effects include all deviations from natural development, for example, killing retardation, defoliation, desiccation, regulation, stunting, tillering, stimulation, leaf burn, dwarfing and the like.

DETAILED DESCRIPTION OF THE INVENTION

The compounds of the present invention are prepared by the reaction of the N-m-aminophenyl succinimides or glutarimides with the appropriate isocyanate or carbamyl chloride. Reactions with the isocyanate or carbamyl chlorides are usually conducted at from about 0° to about 40° C. in a suitable inert solvent such as methylene chloride, acetone, benzene and the like in the presence of an acid acceptor such as pyridine, triethylamine or aqueous bases such as sodium or potassium hydroxides or carbonates. Catalytic quantities of dibutyl tin dilaurate may be used if necessary to increase the reaction rate. These compounds may also be prepared by conversion of the aniline to the isocyanate with phosgene followed by reaction with the appropriate amine in a suitable inert solvent such as those listed above.

The products are usually isolated by filtration or stripping of the solvent under vacuum or when potassium carbonate is used, filtration followed by distillation or the solvent under vacuum.

The appropriate anilines are prepared by the reduction of the N-m-nitrophenylsuccinimides or glutarimides by any of a number of methods such as low pressure catalytic hydrogenation over catalysts such as palladium, platinum or nickel or by chemical reduction with iron and water, zinc and hydrochloric acid or tin and hydrochloric acid depending on the product desired.

The m-nitrophenylsuccinimides or glutarimides may be prepared by the reaction of m-nitro aniline with the appropriate succinoyl or glutaroyl chlorides in an inert solvent in the presence of an acid acceptor such as triethylamine pyridine or aqueous sodium or potassium hydroxides or by reaction with the appropriate acid anhydride followed by elimination of one mole of water by azeotropic distillation or reaction with thionyl chloride followed by treatment with an acid acceptor as above. Preferably, the intermediates are prepared by direct reaction of the succinic or glutaric acid with the aniline followed by azeotropic removal of two moles of water. This latter reaction may be conducted in a water insoluble solvent such as benzene, toluene, xylene or mesitylene at a temperature of from about 80° to about 200° C. The water is collected in a modified Dean Stark apparatus and the product is usually recovered by crystallization from the reaction medium on cooling.

EXAMPLE I

N-m-NITROPHENYL-2,2-DIMETHYLSUCCINIMIDE (INTERMEDIATE)

Sixty-nine grams (0.5 mole) of m-nitroaniline and 76 grams (g.) (0.52 mole) of 2,2-dimethylsuccinic acid were mixed with 200 milliliters (ml.) of xylene and heated to reflux until approximately 20 ml. of water was removed in a modified Dean Stark apparatus. On cooling, the product crystallized from solution. The mixture was diluted with 300 ml. of ether, the solid filtered off, washed with an additional 100 ml. of ether and dried. Yield was 117.5 g. of a product having a melting point (m.p.) of 134°–134.5° C. The product was identified as the title compound by analysis of infrared spectra.

EXAMPLE II

N-m-AMINOPHENYL-2,2-DIMETHYLSUCCINIMIDE (INTERMEDIATE)

One hundred and sixty three g. of N-m-nitrophenyl-2,2-dimethylsuccinimide, as prepared in Example I, was added portion wise at reflux temperature to a mixture of 115 g. of powdered iron, 7 ml. of concentrated HCl, 250 ml. of ethyl alcohol and 200 ml. of water. At completion of addition (approximately one hour), the mixture was allowed to cool to 70° C. and 7 g. of 50% sodium hydroxide was added and the iron oxide was removed by filtration through a Dicalite filter which was washed with several portions of hot ethyl alcohol. Stripping of the filtrate under vacuum yielded 106 g. of a product having a m.p. of 143°–145° C. A portion of the product was recrystallized to a m.p. of 147°–147.5° C. The product was identified as the title compound by analysis of infrared spectra.

EXAMPLE III m-(N-2,2-DIMETHYLSUCCINIMIDO)PHENYL HYDROXYL AMINE (INTERMEDIATE)

Seventy-four and four tenths g. of N-m-nitrophenyl-2,2-dimethylsuccinimide prepared in Example I above was combined with 7 g. of ammonium chloride in 200 ml. of ethyl alcohol and 100 ml. of water. The mixture was heated to 70° C. and 54 g. of powdered zinc was added portion wise to maintain the temperature at reflux. On completion of addition of the zinc dust, the mixture was allowed to cool slightly and filtered hot. The product, crystallized from solution on addition of water, was filtered off and dried. The yield was 34.5 g. of a solid product having a m.p. of 115°–118° C. The product was identified as the title compound by analysis of infrared spectra.

EXAMPLE IV

1(m-N-2,2-DIMETHYLSUCCINIMIDOPHENYL)3-METHYL-3-HYDROXY UREA

Eighteen and seven tenths g. of m(N-2,2-dimethylsuccinimido)phenyl hydroxyl amine, prepared in Example III, and 4.6 g. of methyl isocyanate were combined in 100 ml. of acetone and allowed to stand at room temperature. The acetone was stripped under vacuum giving 22.2 g. of a product. The product after trituration with ether had a m.p. of 140°–142° C.(dec). The product was identified as the title compound by analysis of infrared spectra.

EXAMPLE V

N(m-ISOCYANATOPHENYL)2,2-DIMETHYLSUCCINIMIDE (INTERMEDIATE)

Seventy-three g. of N-m-aminophenyl-2,2-dimethylsuccinimide, as prepared in Example II, was dissolved in 800 ml. of tetrahydrofuran containing 75 g. of triethylamine, cooled in an ice bath, and added to 60 g. of phosgene in 400 ml. of tetrahydrofuran maintained at about 0° C. in a drying and isopropanol bath. The mixture was allowed to warm to room temperature and the triethylamine hydrochloride was filtered off and the tetrahydrofuran removed under vacuum on the rotary evaporator. Yield was 84 g. of material product having a $n_D^{30}$ of 1.5470. The product was identified as the title compound by analysis of infrared spectra and was used without further purification.

EXAMPLE VI

N-m-NITROPHENYL-2-METHYL-2-ETHYLSUCCINIMIDE (INTERMEDIATE)

Sixty-four g. of 2-methyl-2-ethylsuccinic acid was combined with 55.2 g. of m-nitro aniline in 250 ml. of xylene. One-half g. of p-toluene sulfonic acid was added and the mixture heated to reflux under a modified Dean Stark apparatus. After 15–16 ml. of water was removed, the mixture was cooled and the product recovered by filtration. Yield was 78 g. of a product having a m.p. of 88°–89° C. The product was identified as the title compound by analysis of infrared spectra.

EXAMPLE VII

N-m-AMINOPHENYL-2-METHYL-2-ETHYLSUCCINIMIDE (INTERMEDIATE)

Seventy-four g. of N-m-nitrophenyl-2-methyl-2-ethylsuccinimide, as prepared in Example VI, was added portion wise to 60 g. of iron powder, 4 ml. of concentrated HCl, 200 ml. of ethanol and 160 ml. of water at reflux. When addition was complete and the temperature had fallen to 70° C., the mixture was treated with 4 g. of 50% NaOH and filtered immediately. The filtercake was washed with hot ethyl alcohol and the filtrate stripped under vacuum. The product which crystallized on removal of the ethyl alcohol weighed 49 g. when dry and had a m.p. of 100°–102° C. The product was identified as the title compound by analysis of infrared spectra.

EXAMPLE VIII

1(m-N-2-METHYL-2-ETHYLSUCCINIMIDOPHENYL)3,3-DIMETHYL UREA

Seven g. of N-m-aminophenyl-2-methyl-2-ethylsuccinimide, as prepared in Example VI, was added to 4.2 g. of powdered $K_2CO_3$ and 3.2 g. of dimethyl carbamyl chloride in 50 ml. of acetone. The stirred mixture was heated at reflux for six to eight hours and poured into water. The product was extracted with methylene chloride, dried and stripped under vacuum. Yield was 7 g. of an oil. The infrared spectrum revealed unreacted starting material which was removed by washing with 5% HCl solution. The yield of product was 1.8 g. of an oil having a $n_D^{30}$ of 1.5397. The product was identified as the title compound by analysis of infrared spectra.

EXAMPLE IX

1(m-N-2,2-DIMETHYLSUCCINIMIDOPHENYL)3-METHYL-3-METHOXY UREA

Six g. of O,N-dimethylhydroxylamine hydrochloride was slurried with 5 ml. of 50% sodium hydroxide solution and 25 ml. of benzene. Magnesium sulfate was added to take up water and the dried benzene solution was added to 9.8 g. of N(m-isocyanatophenyl) 2,2-dimethylsuccinimide in 100 ml. of acetone. The mixture was heated at reflux for an hour and stripped under vacuum. Yield was 12.5 g. of an oil, having a $n_D^{30}$ of 1.5440. The product was identified as the title compound by analysis of infrared spectra.

EXAMPLE X

1(m-N-2,2-DIMETHYLSUCCINIMIDOPHENYL)3-METHYL UREA

Three g. of methyl isocyanate was added to 8.7 g. of N-m-aminophenyl-2,2-dimethylsuccinimide, as prepared in Example II, in 100 ml. of acetone. The mixture was heated at reflux for one to two hours and stripped under vacuum. The yield was 11.4 g. of an oil having a $n_D^{30}$ of 1.5473. The product was identified as the title compound by analysis of infrared spectra.

EXAMPLE XI

1(m-N-2,2-DIMETHYLSUCCINIMIDOPHENYL)3,3-DIMETHYL UREA

Six g. of powdered potassium carbonate was added to 4.5 g. of dimethyl carbamyl chloride and 8.7 g. of N-m-aminophenyl-2,2-dimethylsuccinimide, as prepared in Example II, in 100 ml. of acetone. The stirred mixture was heated at reflux for four to six hours and poured into water. The product was extracted with methylene chloride, dried and stripped under vacuum. The yield was 9 g. of an oil having a $n_D^{30}$ of 1.5643. The product was identified as the title compound by analysis of infrared spectra.

EXAMPLE XII

1(m-N-3,3-DIMETHYLGLUTARIMIDOPHENYL)3-METHYL UREA

Nine and three-tenths g. of N-m-aminophenyl-3,3-dimethylglutarimide was dissolved in 100 ml. of acetone. Three g. of methyl isocyanate was added and the mixture refluxed for one hour. The solvent was removed under vacuum giving 12 g. of a product having a m.p. of 192°–195° C. The product was identified as the title compound by analysis of infrared spectra.

In the following table, the compounds of Examples IV and VIII-XII ar listed together with nine additional examples which were prepared in a manner analogous to that described above, starting with the appropriate materials. The compounds in the table are representative of those embodied in the present invention.

TABLE 1

| Compound Number | R | $R_1$ | $R_2$ | $R_3$ | m | n | Physical Properties |
|---|---|---|---|---|---|---|---|
| 1 | H— | H— | $CH_3$— | $CH_3$— | 0 | 1 | $n_D^{30}$ 1.5473 |
| 2 | H— | $CH_3$— | $CH_3$— | $CH_3$— | 0 | 1 | $n_d^{30}$ 1.5643 |
| 3 | H— | H— | $C_4H_9$— | $CH_3$— | 0 | 1 | $n_D^{30}$ 1.5403 |
| 4 | H— | H— | $CH_3$— | $CH_3$— | 0 | 2 | $n_D^{30}$ 1.5410 |
| 5 | H— | $CH_3$— | $CH_3$— | $CH_3$— | 0 | 2 | glassy material |
| 6 | H— | H— | $CH_3$— | $CH_3$— | 1 | 1 | m.p. 191–194° C. |
| 7 | H— | $CH_3$— | $CH_3$— | $CH_3$— | 1 | 1 | $n_D^{30}$ 1.5460 |
| 8 | OH— | H— | $CH_3$— | $CH_3$— | 0 | 1 | m.p. 140–142° C. |
| 9 | H— | $CH_3$— | $CH_3O$— | $CH_3$— | 0 | 1 | $n_D^{30}$ 1.5440 |
| 10 | H— | H— | $CH_3$— | $C_2H_5$— | 0 | 1 | $n_D^{30}$ 1.5338 |
| 11 | H— | $CH_3$— | $CH_3$— | $C_2H_5$— | 0 | 1 | $n_D^{30}$ 1.5392 |
| 12 | H— | H— | $C_4H_9$— | $C_2H_5$— | 0 | 1 | $n_D^{30}$ 1.5423 |
| 13 | H— | H— | $CH_3$— | H— | 0 | 1 | $n_D^{30}$ 1.5639 |
| 14 | H— | $CH_3$— | $CH_3$— | H— | 0 | 1 | $n_D^{30}$ 1.5325 |
| 15 | H— | H— | $C_4H_9$— | H— | 0 | 1 | $n_D^{30}$ 1.5430 |

Herbicidal Screening Test

As previously mentioned, the novel N-m-phenyl-succinimide and glutarimide derivatives herein described are phytotoxic compounds which are useful and valuable in controlling various plant species. Compounds of this invention are tested as herbicides in the following manner.

Pre-Emergence Herbicide Screening Test

On the day preceding treatment, seeds of seven different weed species are planted in individual rows using one species per row across the width of the flat. The seeds used are hairy crabgrass (*Digitaria sanguinalis* (L.) Scop.), yellow foxtail (*Setaria glauca* (L.) Beauv.), watergrass (*Echinochloa crusgalli* (L.) Beauv.), California red oat (*Avena sativa* (L.)), redroot pigweed (*Amaranthus retroflexus* (L.), Indian mustard (*Brassica juncea* (L.) Coss.) and curly dock (*Rumex crispus* (L.). Ample seeds are planted to give about 20 to 50 seedlings per row, after emergence, depending on the size of the plants. The flats are watered after planting. The spraying solution is prepared by dissolving 50 milligrams (mg.) of the test compound in 3 ml. of a solvent, such as acetone, containing 1% Tween 20 ® (polyoxyethylene sorbitan monolaurate). The following day each flat is sprayed at the rate of 20 pounds of the candidate compound per 143 gallons of solution per acre. An atomizer is used to spray the solution on soil surface. The flats are placed in a greenhouse at 80° F. and watered regularly. Two weeks later the degree of weed control is determined by comparing the amount of germination and growth of each weed in the treated flats with weeds in several untreated control flats.

The rating system is as follows:
- — = no significant injury (0–15% control)
- + = slight injury (25–35% control)
- + + = moderate injury (55–65% control)
- + + + = severe injury or death (85–100% control)

An activity index is used to represent the total activity on all seven weed species. It is the sum of the number of plus marks, so that an activity index of 21 represents complete control of all seven weeds. The results of this test are reported in Table 2.

Post-Emergence Herbicide Screening Test

Seeds of five weed species including hairy crabgrass, watergrass, wild oats, Indian mustard, and curly dock and one crop Pinto beans (*Phaseolus vulgaris*), are planted in flats as described above for pr-emergence screening. The flats are placed in the greenhouse at 72°-85° F. and watered daily with a sprinkler. About 10-14 days after planting when the primary leaves of the bean plant are almost fully expanded and the first trifoliate leaves are just starting to form, the plants are sprayed. The spray is prepared by weighing out 50 mg. of the test compound, dissolving it in 5 ml. of acetone containing 1% Tween 20 ® (polyoxyethylene sorbitan monolaurate) and then adding 5 ml. of water. The solution is sprayed on the foliage using an atomizer. The spray concentration is 0.5% and the rate would be approximately 20 lb/acre if all of the spray were retained on the plant and the soil, but some spray is lost so it is estimated that the application rate is approximately 12.5 lb/acre.

Beans are used to detect defoliants and plant growth regulators. The beans are trimmed to two or three plants per flat by cutting off the excess weaker plants several days before treatment. The treated plants are placed back in the greenhouse and care is taken to avoid sprinkling the treated foliage with water for three days after treatment. Water is applied to the soil by means of a slow stream from a watering hose taking care not to wet the foliage.

Injury rates are recorded 14 days after treatment. The rating system is the same as described above for the pre-emergence test where (−), (+), (++) and (+++) are used for the different rates of injury and control. The injury symptoms are also recorded. The maximum activity index for complete control of all the species in the post-emergence screening test is 18 which represents the sum of the plus marks obtained with the six plant species used in the test. The herbicide activity index for compounds 1–12 is shown in Table 2.

TABLE 2

Herbicidal Activity - Screening Results

| Compound Number | Pre-emergence | Post-emergence |
|---|---|---|
| 1 | 20 | 16 |
| 2 | 20 | 17 |
| 3 | 20 | 17 |
| 4 | 6 | 7 |
| 5 | 7 | 7 |
| 6 | 20 | 16 |
| 7 | 20 | 16 |
| 8 | 19 | 18 |
| 9 | 20 | 18 |
| 10 | 17 | 16 |
| 11 | 17 | 16 |
| 12 | 16 | 16 |

Pre-Emergence Herbicide Screening Test

Using an analytical balance, 20 mg. of the compound to be tested is weighed out on a piece of glassine weighing paper. The paper and compound are placed in a 30 ml. wide-mouth bottle and 3 ml. of acetone containing 1% Tween 20 ® (an emulsifying agent defined as a polyoxyethylene sorbitan monolaurate) is added to dissolve the compound. If the material is not soluble in acetone, another solvent such as water, alcohol or dimethylformamide (DMF) is used instead. When dimethylformamide is used, only 0.5 ml. or less is used to dissolve the compound and then another solvent is used to make the volume up to 3 ml. The 3 ml. of solution is sprayed uniformly on the soil contained in a small Fiber flat one day after planting weed seeds in the flat of soil. A No. 152 DeVilbiss atomizer is used to apply the spray using compressed air at a pressure of 5 lb/sq inch. The rate of application is 8 lb/acre and the spray volume is 143 gallons/acre.

On the day preceding treatment, the Fiber flat, which is 7 inches long, 5 inches wide an 2.75 inches deep is filled to a depth of 2 inches with loamy sand soil. Seeds of seven different weed species are planted in individual rows using one species per row across the width of the flat. The seeds are covered with soil so that they are planted at a depth of 0.5 inch. The seeds used are hairy crabgrass (*Digitaria sanguinalis*), yellow foxtail (*Setaria glauca*), redroot pigweed (*Amaranthus retroflexus*), Indian mustard (*Brassica juncea*), curly dock (*Rumex crispus*), watergrass (*Echinochloa crusgalli*), and red oat (*Avena sativa*). Ample seeds are planted to give about 20 to 50 seedlings per row after emergence depending on the size of the plants.

After treatment, the flats are placed in the greenhouse at a temperature of 70° to 85° F. and watered by sprinkling. Two weeks after treatment the degree of injury or control is determined by comparison with untreated check plants of the same age. The injury rating from 0 to 100% is recorded for each species as percent control with 0% representing no injury and 100% representing complete injury.

Post-Emergence Herbicide Screening Test

Seeds of six plant species, including hairy crabgrass, watergrass, red oat, mustard, curly dock and Pinto beans (*Phaseolus vulgaris*) are planted in the Fiber flats as described above for pre-emergence screening. The flats are placed in the greenhouse at 70° to 85° F. and watered daily with a sprinkler. About 10 to 14 days after planting when the primary leaves of the bean plants are almost fully expanded and the first trifoliate leaves are just starting to form, the plants are sprayed. The spray is prepared by weighing out 20 ml. of the test compound, dissolving it in 5 ml. of acetone containing 1% Tween 20 ® (an emulsifying agent defined as a polyoxyethylene sorbitan monolaurate) and then adding 5 ml. of water. The solution is sprayed on the foliage using a No. 152 DeVilbiss atomizer at an air pressure of 5 lb/sq inch. The spray concentration is 0.2 and the rate is 8 lb/acre. The spray volume is 476 gallons/acre. Injury ratings are recorded 14 days after treatment. The rating system is the same as described above in the pre-emergence test.

The results of these tests for compounds 13–15 are shown in Table 3.

TABLE 3

| Compound Number | Percent Control* at 8 lb/A | |
|---|---|---|
| | Pre-emergence | Post-emergence |
| 13 | 34 | 85 |
| 14 | 79 | 92 |
| 15 | 40 | 85 |

The compounds of the present invention are useful as herbicides in controlling the growth of undesirable vegetation by pre-emergence or post-emergence application to the locus where control is desired. The compounds are generally embodied in formulations suitable for convenient application. In general, such formulations will contain inert or occasionally active ingredients or diluent carriers in addition to the active compound. Examples of such ingredients or carriers are water, organic solvents, dust carriers, granular carriers, surface active agents, oil and water, water in oil emulsions, wetting agents, dispersing agents and emulsifying agents. The herbicidal formulations generally take the form of dusts, wettable powders, granules, solutions or emulsifiable concentrates.

Dusts are free-flowing powder compositions containing the herbicidal compound impregnated on a particular carrier. The particle size of the carrier is usually in the range of from about 30 to 50 microns. Examples of suitable carriers are talc, bentonite, diatomaceous earth and pyrophyllite. Anticaking and antistatic agents can be added, if desired. The composition generally contains up to 50% by weight of active ingredient.

Wettable powders are finely divided compositions comprising a particulate carrier impregnated with the herbicidal compound and additionally contain one or more surface active agents. The surface active agent promotes rapid dispersion of the powder in aqueous medium to form suitable, sprayable suspensions. A wide variety of surface active agents can be used, for example, long chain fatty alcohols and alkali metal salts of the sulfated fatty alcohols; salts of sulfonic acid; esters of long chain fatty acids; and polyhydric alcohols, in which the alcohol groups are free, omega-substituted polyethylene glycols of relatively long chain length. A list of surface active agents suitable for use in agriculture formulations can be found in Pesticide Formulations by Wade Van Valkenburg, Marcel Dekker, Inc., N.Y. 1973 at pages 79–84.

Granules comprise the herbicidal compound impregnated on a particulate inert carrier having a particle size of about 1 to 2 ml. in diameter. The granules can be made by spraying a solution of the active ingredient in a volatile solvent onto the granular carrier. Suitable carriers in preparation of granules include clay, vermiculite, sawdust, granular carbon and the like.

The herbicidal compounds can also be applied to the soil in the form of a solution in a suitable solvent. Solvents frequently used in herbicidal formulations include kerosene, fuel oil, xylene, petroleum fractions with boiling ranges above xylene, and aromatic petroleum fractions rich in methylated naphthalenes.

Emulsifiable concentrates consist of an oil solution of the herbicide along with an emulsifying agent. Prior to use the concentrate is diluted with water to form a suspended emulsion of oil droplets. The emulsifiers used are usually a mixture of anionic and nonionic surfactants. Other additives such as spreading agents and stickers can be included in the emulsifiable concentrate.

The formulations described above, employing phytotoxic or herbicidally effective amounts of the compounds described herein, are applied to the loci where control is desired in any conventional manner. The loci referred to above include soil, seeds, seedlings and the actual plants. Dusts and liquid compositions can be applied by the use of power dusters, boom and hand sprayers and spray dusters. The compositions can also be applied from airplanes as dusts or sprays because they are effective in very low dosages. In order to modify or control growth of germinating seeds or emerging seedlings, as a typical example, the dust and liquid compositions are applied to the soil according to conventional methods and are distributed in the soil to a depth of at least one-half inch below the soil surface. It is not necessary that the phytotoxic compositions be admixed with the soil particles. Instead, these compositions can be applied merely by spraying or sprinkling the surface of the soil. The phytotoxic compositions of this invention can also be applied by addition or irrigation water supplied to the field to be treated. This method of application permits the penetration of the compositions into the soil as the water is absorbed therein. Dust compositions, granular compositions or liquid formulations applied to the surface of the soil by conventional means such as discing, dragging or mixing operations.

The phytotoxic compositions of this invention can also contain other additaments, for example, fertilizers, pesticides and the like, used as adjuvants or in combination with any of the above-described adjuvants. Other phytotoxic compounds useful in combination with the above-described compounds include, for example, 2,4-dichlorophenoxyacetic acids, 2,4,5-trichlorophenoxyacetic acid, 2-methyl-4-chlorophenoxyacetic acid, and the salts, esters and amides thereof; triazine derivatives, such as 2,4-bis(3-methoxy-propylamino)-6-methyl-thio-s-triazine; 2-chloro-4-ethylamino-6-isopropylamino-3-triazine, and 2-ethyl-amino-4-isopropylamino-6-methyl-mercapto-s-triazine, urea derivatives such as 3-(3,4-dichlorophenyl)-1,1-dimethyl urea, and acetamides such as N,N-di-allyl-α-chloroacetamide, N-(α-chloroacetyl) hexamethyleneamine, and N,N-diethyl-α-bromoacetamide, and the like; benzoic acids such as 3-amino-2,5-dichlorobenzoic; S-ethyl-dipropylthiocarbamate; S-ethyl hexahydro-1H-azepine-1-carbothioate and the like. Fertilizers useful in combination with the active ingredients include, for example, ammonium nitrate, urea and superphosphate. Other useful additaments include materials in which plant organisms take root and grow, such as compost, manure, humus, sand and the like.

The amount of a compound of the present invention which constitutes a phytotoxic or herbicidally effective amount depends upon the nature of the seeds or plants to be controlled. The rate of application of active ingredient varies from about 0.01 to about 50 pounds per acre, with the actual amount used depending on the overall cost and the desired results. It will be readily apparent to one skilled in the art that compounds exhibiting lower herbicidal activity will require a higher dosage rate for the same degree of control than more active compounds.

What is claimed is:

1. A compound having the formula

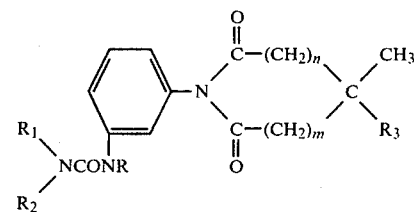

wherein R is hydrogen or hydroxyl, $R_1$ is selected from the group consisting of methyl and hydrogen; $R_2$ is selected from the group consisting of methyl, ethyl, propyl and butyl and methoxy; $R_3$ is selected from the group consisting of hydrogen, methyl and ethyl; m is 0 or 1; and n is 1 or 2 provided that m+n equals 2.

2. A compound of claim 1 in which R is H—; $R_1$ is H—; $R_2$ is $CH_3$—; $R_3$ is $CH_3$—; m is 0; and n is 2.

3. A compound of claim 1 in which R is H—; $R_1$ is $CH_3$—; $R_2$ is $CH_3$—; $R_3$ is $CH_3$—; m is 0; and n is 2.

4. A compound of claim 1 in which R is H—; $R_1$ is H—; $R_2$ is $CH_3$—; $R_3$ is $CH_3$—; m is 1; and n is 1.

5. A compound of claim 1 in which R is H—; $R_1$ is $CH_3$—; $R_2$ is $CH_3$—; $R_3$ is $CH_3$—; m is 1 and n is 1.

6. A composition of matter comprising
(1) a herbicidally effective amount of the compound having the formula

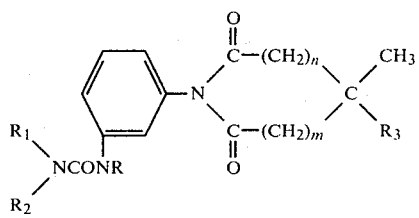

wherein R is hydrogen or hydroxyl, $R_1$ is selected from the group consisting of methyl and hydrogen; $R_2$ is selected from the group consisting of methyl, ethyl, propyl and butyl and methoxy; $R_3$ is selected from the group consisting of hydrogen, methyl and ethyl; m is 0 or 1; and n is 1 or 2 provided that m+n equals 2, and
(2) an inert carrier.

7. A composition of claim 6 in which R is H—; $R_1$ is H—; $R_2$ is $CH_3$—; $R_3$ is $CH_3$—; m is 0; and n is 2.

8. A composition of claim 6 in which R is H—; $R_1$ is $CH_3$—; $R_2$ is $CH_3$—; $R_3$ is $CH_3$—; m is 0; and n is 2.

9. A composition of claim 6 in which R is H—; $R_1$ is H—; $R_2$ is $CH_3$—; $R_3$ is $CH_3$—; m is 1 and n is 1.

10. A composition of claim 6 in which R is H—; $R_1$ is $CH_3$—; $R_2$ is $CH_3$—; $R_3$ is $CH_3$—; m is 1; and n is 1.

11. A method of controlling undesirable vegetation comprising applying to the locus thereof a herbicidally effective amount of the compound having the formula

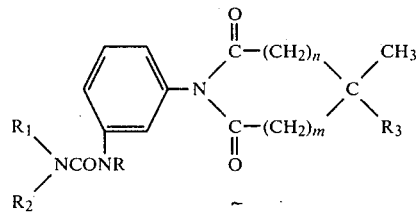

wherein R is hydrogen or hydroxyl, $R_1$ is selected from the group consisting of methyl and hydrogen; $R_2$ is selected from the group consisting of methyl, ethyl, propyl and butyl and methoxy; $R_3$ is selected from the group consisting of hydrogen, methyl and ethyl; m is 0 or 1; and n is 1 or 2 provided that m+n equals 2.

12. A method of claim 11 in which R is H—; $R_1$ is H—; $R_2$ is $CH_3$—; $R_3$ is $CH_3$—; m is 0; and n is 2.

13. A method of claim 11 in which R is H—; $R_1$ is $CH_3$—; $R_2$ is $CH_3$—; $R_3$ is $CH_3$—; m is 0; and n is 2.

14. A method of claim 11 in which R is H—; $R_1$ is H—; $R_2$ is $CH_3$—; $R_3$ is $CH_3$—; m is 1; and n is 1.

15. A method of claim 11 in which R is H—; $R_1$ is $CH_3$—; $R_2$ is $CH_3$—; $R_3$ is $CH_3$—; m is 1; and n is 1.

* * * * *